United States Patent [19]

DuMont et al.

[11] 4,010,756

[45] Mar. 8, 1977

[54] HEART PACER LEAD WIRE WITH BREAK-AWAY NEEDLE

[75] Inventors: Jacques DuMont, Asnieres; Jacques Romagne, Les Essarts le Roi, both of France

[73] Assignee: Ethicon, Inc., Somerville, N.J.

[22] Filed: Feb. 13, 1976

[21] Appl. No.: 657,897

[30] Foreign Application Priority Data

Feb. 14, 1975 France .............................. 75.04710

[52] U.S. Cl. .............................. 128/404; 128/335.5; 128/339; 128/419 P

[51] Int. Cl.² .......................................... A61N 1/04

[58] Field of Search ................ 128/335.5, 339, 404, 128/416, 418, 419 P

[56] References Cited

UNITED STATES PATENTS

| | | | |
|---|---|---|---|
| 3,035,583 | 5/1962 | Hirsch et al. | 128/418 |
| 3,125,095 | 3/1964 | Kaufman et al. | 128/419 P |
| 3,416,534 | 12/1968 | Quinn | 128/418 |
| 3,474,791 | 10/1969 | Bentov | 128/418 |
| 3,540,452 | 11/1970 | Usher et al. | 128/335.5 |

*Primary Examiner*—William E. Kamm
*Attorney, Agent, or Firm*—Wayne R. Eberhardt

[57] ABSTRACT

A surgical electrode consisting of an insulated stainless steel wire having needles conductively affixed at one or both ends, at least one needle having a blunt end with a straight shank and having a weakened zone between the straight shank end and the opposite pointed end of the needle whereby the pointed end may be snapped off and the straight shank used as an electrical jack for connection to a pacemaker or similar electric current generating or monitoring device. The electrodes are particularly useful as temporary heart pacer electrodes for cardiac stimulation during and after surgical operations.

10 Claims, 4 Drawing Figures

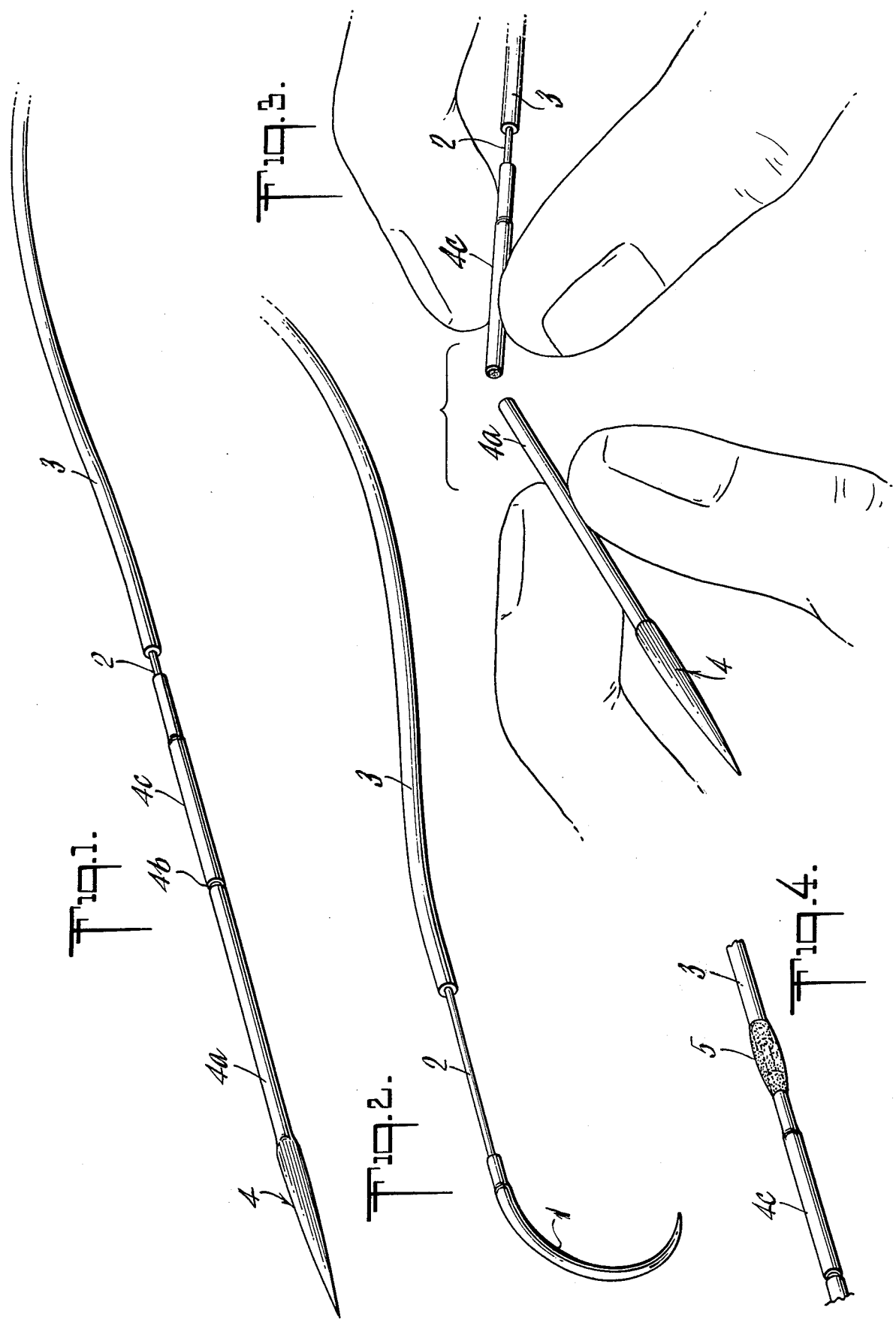

HEART PACER LEAD WIRE WITH BREAK-AWAY NEEDLE

BACKGROUND OF THE INVENTION

1. Field of Invention

This invention relates to surgical electrodes, and more particularly to an improvement in needled surgical electrodes to facilitate the attachment of the electrode to electrical generating or monitoring devices.

2. Description of Prior Art

Surgical electrodes for use as heart pacer electrodes are well known in the medical profession. In general, such electrodes are constructed of a number of fine, stainless steel wires twisted together to form a single, flexible, multifilament electrode wire. The major portion of the wire is insulated with a polyethylene, polytetrafluoroethylene, silicone, nylon, or other non-conducting coating, with a short length of wire at either end left uninsulated. To one uninsulated end of the electrode wire there is attached by swaging or other means a fine curved needle for piercing the heart tissue to place the uninsulated end of the electrode in the myocardium. At the other end of the electrode wire is affixed a Keith-type cutting needle for piercing the thoracic wall to lead the electrode to an outer point for connection with the pacemaker. Once the electrode has been properly positioned, the needles are clipped off and the uninsulated end of the electrode is ready for attachment to the pacemaker as required for stimulating or regulating the beating of the heart.

Insulated stainless steel sutures and their application as heart pacer electrode wires are described generally in U.S. Pat. Nos. 3,035,583 and 3,125,095, which patents are incorporated herein by reference. Other conductive insulated sutures which can be employed in the practice of the present invention are disclosed in U.S. Pat. No. 3,847,156 and British Patent No. 1,258,688 which are also incorporated herein by reference.

The electrodes of the prior art all have a common disadvantage in that when the electrode has been positioned for heart stimulation, the needle on the end exterior to the body must be clipped off and the bare stainless steel wire then attached in electrical contact to the pacemaker unit. These steps of needle removal and wire attachment are separate, time consuming acts at a critical stage of the heart surgery. Moreover, upon repeated attachment, removal and reattachment, the ends of the stainless steel wire may fray and become difficult to work with. The present invention works an improvement over the prior art by simplifying the attachment, removal and reattachment of the electrode to the pacemaker.

It is accordingly an object of the present invention to provide a surgical electrode having a needle, the sharpened end of which can be removed without cutting. It is a further object of this invention to provide a surgical electrode which is quickly and easily attached to a pacemaker after removal of the sharpened end of the needle. It is yet a further object of this invention to provide surgical electrodes having electrical connecting means adapted for specific electrical devices.

SUMMARY

A conventional surgical electrode wire is equipped with a specially designed needle having a sharp or pointed end, an opposite blunt end, and a weakened zone intermediate said ends with the portion of the needle extending from said weakened zone to said blunt end being substantially straight. The blunt end of the needle is attached to and in electrical contact with the conductive electrode wire. Following placement of the electrode in the patient, the needle is broken by application of a bending moment about the weakened zone whereupon the pointed end is discarded and the straight blunt end remaining attached to the electrode wire is conveniently connected to an electrical stimulation or monitoring device.

BRIEF DESCRIPTION OF DRAWING

FIG. 1 is the end of the electrode intended for attachment to the pacemaker and having the special needle of the instant invention.

FIG. 2 is the end of the electrode intended for attachment to the heart and having a fine, curved needle for piercing the myocardium.

FIG. 3 shows the straight needle shaft remaining after the pointed end of the needle has been snapped off.

FIG. 4 shows a preferred embodiment of the surgical electrode wherein the insulation is continuous from the needle shank to the suture wire.

DESCRIPTION OF PREFERRED EMBODIMENTS

The surgical electrodes of the present invention have at least one eyeless needle conductively attached to the electrode wire and embodying the novel features as described herein. Specifically, the novel needles of the present invention are characterized by having a sharp or pointed end, an opposite blunt end with an axial opening therein for attachment of an electrode wire, and a weakened zone intermediate said ends with the portion of the needle extending from said weakened zone to said blunt end being substantially straight and at least about 1 cm. long. With specific reference to FIG. 1 of the drawing, needle 4 has a straight shank end 4 (c) attached to and in electrical contact with wire 2, preferably by swaging. Pointed end 4 (a) of needle 4 has a cutting edge designed for piercing the thoracic wall of the patient. Intermediate end 4 (a) and end 4 (c) is weakened zone 4 (b), preferably formed by machining a groove in the needle to reduce needle diameter. In general, a machined groove in the needle is preferred for ease of identification and location of the weakened zone. Alternatively, the needle may be weakened by forming a groove by rotating the needle in contact with a cutting wheel, or by cutting a notch or forming a crimp on one or both sides of the needle. A weakened zone may also be obtained by modification of crystalline structure through heat treating by drawing the needle to create a necked down segment, or by other convenient means.

When the electrode has been positioned in the patient and is ready for attachment to the pacemaker device, the needle is snapped at zone 4 (b) as shown in FIG. 3 by applying a bending moment about zone 4 (b). End 4 (a) is discarded while end 4 (c) with attached electrode is readily inserted into a properly sized receptacle in the pacemaker device. Needle end 4 (c) presents a unified structure which may be quickly and readily attached, removed, and reattached to the pacemaker as required without encountering frayed ends characteristic of a bare, multifilament stainless steel wire.

Needle 4 is conventionally straight and of a circular cross-section. For purposes of the instant invention however, the configuration of pointed end 4 (a) is immaterial and it may be curved, straight, or of any desired configuration. End 4 (c) is preferably straight for convenient insertion into the connecting receptacle on the pacemaker, but end 4 (c) may be of any desired cross-sectional configuration. While a circular cross-section is generally preferred, end 4 (c) may be triangular, rectangular, or square and such cross-sections may be particularly useful where the electrode is intended to be connected to a particular electrical device, and the needle is desirably designed to fit that particular device and no other.

Since needle shaft 4 (c) is used for making electrical connection with the electrical device, insulation 3 of wire 2 may extend up to or even over the end of needle 4. Abutting the insulation to the blunt end of the needle and sealing the joint as shown in FIG. 4 has the advantage of providing a smooth, continuous and sealed exterior surface to facilitate threading the electrode through the thoracic wall and to exclude contamination from the interior of the electrode. In the sutures of the prior art, it has been necessary to provide a segment of uninsulated suture adjacent the needle to allow for electrical connection to the pacemaker after the needle has been clipped off the wire, or to take an extra step of stripping insulation from the wire to provide an electrical connection.

The end of the electrode intended for connection to the heart has a fine, curved needle attached to a length of uninsulated wire as shown in FIG. 2. The needle is passed through the ventricular myocardium and the wire is drawn through until the insulated portion of the electrode abuts the surface of the heart. The electrode is anchored to the heart and the needle and excess suture wire are then clipped off leaving a length of uninsulated wire within the myocardium and in electrical contact therewith.

The special, break-away needles of the present invention are illustrated by the following example. A 420 stainless stell Keith-type cutting needle 6.8 cm. long and 34 mm. in diameter was machine grooved about the circumference of the needle at a point 2 cm. from the blunt end. The groove was approximately 8 mm. wide and 4 mm. deep. A size 2-0 insulated, multi-filament stainless steel wire having an uninsulated end was attached to the needle by swaging in a pre-drilled hole. The needle was easily snapped at the groove in a clean, square break by the application of a bending moment of approximately 1 inch-pound at the groove site. The straight shank remaining attached to the electrode wire was suitable for inserting into an electrical connection on a pacemaker device. A similar but ungrooved Keith-type needle bent to an angle of 60° without breaking by the application of approximately 2.3 inches pounds of force.

The grooved or otherwise weakened zone of the needle may be located at any convenient distance from the blunt end of the needle. The length of the needle shaft remaining after the pointed end is snapped off should be sufficient for grasping and inserting into the electrical receptacle. In general, the weakened zone will preferably be a distance of at least 1 cm. from either end of needle, and most preferably from about 2 to about 3 cm. When the distance between the weakened zone and either end is less than about 1 cm., it is difficult to grasp the needle for breaking, and when the severed needle shank is less than 1 cm. long, it is difficult to handle and insert into the electrical receptacle.

The preceding Figures and description are illustrative of the preferred embodiment of the present invention employing a Keith-type needle, but the invention is not limited thereto. Any needle having a straight shank portion may be used. Since the needles according to the instant invention are required to be in electrical contact with the electrode wire, the needles are preferably drilled or channelled needles attached by swaging. Other methods of electrically conductive attachment such as soldering or welding can of course be utilized.

What is claimed is:

1. In a surgical electrode comprising
   a. an electrically conductive wire,
   b. a needle attached to and in electrical contact with said wire and having a substantially straight shank portion adjacent the point of attachment to said wire, and
   c. a non-conductive coating over the exterior surface of the wire electrically insulating said wire over a major portion of the length thereof,
   the improvement comprising providing a weakened zone in the needle adjacent the straight shank portion of said needle whereby said needle may be readily broken at said weakened zone.

2. An electrode of claim 1 wherein said weakened zone is at least about 1 cm. from either end of said needle.

3. An electrode of claim 1 wherein the surface of said needle at said weakened zone defines a groove machined in the circumference of said needle.

4. An electrode of claim 1 wherein the surface of the needle at said weakened zone defines a groove formed in the circumference of said needle.

5. An electrode of claim 1 wherein the surface of the needle at said weakened zone defines a necked down segment of the needle.

6. An electrode of claim 1 wherein said non-conductive coating over the exterior of surface of the wire substantially abuts the needle.

7. An electrode of claim 1 wherein the non-conductive coating over the exterior surface of the wire is continuous from the surface of the needle.

8. An electrode of claim 1 wherein said conductive wire is a multifilament stainless steel strand.

9. An electrode of claim 1 wherein said non-conductive coating is polyethylene, polytetrafluoroethylene, silicone or nylon.

10. In a surgical electrode comprising
    a. an electrically conductive wire,
    b. a first eyeless needle and a second eyeless needle attached to either end of said wire and in electrical contact therewith, at least one eyeless needle having a substantially straight shank portion at least about 1 cm. long adjacent the point of attachment to said wire, and
    c. a non-conductive coating over the exterior surface of the wire electrically insulating said wire over a major portion of the length thereof,
    the improvement comprising providing in the needle having a straight shank portion a weakened zone adjacent said straight shank portion whereby the needle may be readily broken by a bending moment applied about the weakened zone.

* * * * *

UNITED STATES PATENT AND TRADEMARK OFFICE
CERTIFICATE OF CORRECTION

PATENT NO. : 4,010,756

DATED : March 8, 1977

INVENTOR(S) : Jacques DuMont, Jacques Romagne

It is certified that error appears in the above-identified patent and that said Letters Patent are hereby corrected as shown below:

At Column 3, Line 40, "34 mm." should be -- 34 mils (0.86 mm.) --.

At Column 3, Line 42, "8 mm." should be -- 8 mils (0.2 mm.) --.

At Column 3, Line 43, "4 mm." should be -- 4 mils (0.1 mm.) --.

Signed and Sealed this

Twenty-sixth Day of June 1979

[SEAL]

Attest:

RUTH C. MASON
Attesting Officer

DONALD W. BANNER
Commissioner of Patents and Trademarks

REEXAMINATION CERTIFICATE (140th)
United States Patent [19]

DuMont et al.

[11] B1 4,010,756

[45] Certificate Issued Nov. 29, 1983

[54] HEART PACER LEAD WIRE WITH BREAK-AWAY NEEDLE

[75] Inventors: Jacques DuMont, Asnieres; Jacques Romagne, Les Essarts le Roi, both of France

[73] Assignee: Ethicon, Inc., Somerville, N.J.

Reexamination Request:
No. 90/000,284, Nov. 8, 1982

Reexamination Certificate for:
Patent No.: 4,010,756
Issued: Mar. 8, 1977
Appl. No.: 657,897
Filed: Feb. 13, 1976

Certificate of Correction issued Jun. 26, 1979.

[30] Foreign Application Priority Data

Feb. 14, 1975 [FR] France .................. 75 04710

[51] Int. Cl.$^3$ .................................. A61N 1/04
[52] U.S. Cl. ...................... 128/786; 128/335.5; 128/339; 128/419 P
[58] Field of Search ............ 128/335.5, 339, 419 P, 128/784, 785, 786

[56] References Cited

U.S. PATENT DOCUMENTS

| | | | |
|---|---|---|---|
| 1,960,117 | 5/1934 | Lydeard | 128/339 |
| 2,240,330 | 4/1941 | Flagg et al. | 128/339 |
| 2,669,754 | 2/1954 | Chadbourne | 18/59 |
| 2,778,097 | 1/1957 | Berg | 29/193.5 |
| 3,035,583 | 5/1962 | Hirsch et al. | 128/335.5 |
| 3,125,095 | 3/1964 | Kaufman et al. | 128/335.5 |
| 3,244,174 | 4/1966 | Wesbey et al. | 128/418 |
| 3,320,954 | 5/1967 | Cowley | 128/218 |
| 3,416,534 | 12/1968 | Quinn | 128/418 |
| 3,474,791 | 10/1969 | Bentov | 128/418 |
| 3,516,412 | 6/1970 | Ackerman | 128/418 |
| 3,533,403 | 10/1970 | Woodson | 128/2.06 |
| 3,540,452 | 11/1970 | Usher et al. | 128/335.5 |
| 3,799,169 | 3/1974 | Beroff et al. | 128/339 |
| 3,847,156 | 11/1974 | Trombia | 128/335.5 |
| 3,875,946 | 4/1975 | Duncan | 128/339 |
| 3,890,975 | 6/1975 | McGregor | 128/339 |
| 3,949,756 | 4/1976 | Ace | 128/339 |

FOREIGN PATENT DOCUMENTS

| | | | |
|---|---|---|---|
| 693774 | 9/1964 | Canada | 128/73 |
| 1132754 | 7/1962 | Fed. Rep. of Germany . | |
| 704311 | 4/1966 | Italy . | |
| 1258688 | 12/1971 | United Kingdom . | |

*Primary Examiner*—William E. Kamm

[57] ABSTRACT

A surgical electrode consisting of an insulated stainless steel wire having needles conductively affixed at one or both ends, at least one needle having a blunt end with a straight shank and having a weakened zone between the straight shank end and the opposite pointed end of the needle whereby the pointed end may be snapped off and the straight shank used as an electrical jack for connection to a pacemaker or similar electric current generating or monitoring device. The electrodes are particularly useful as temporary heart pacer electrodes for cardiac stimulation during and after surgical operations.

REEXAMINATION CERTIFICATE ISSUED UNDER 35 U.S.C. 307.

HEART PACER LEAD WIRE WITH BREAK-AWAY NEEDLE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 10 are determined to be patentable as amended:

Claims 2-9, dependent on amended claims, are determined to be patentable.

New claims 11-14 are added and determined to be patentable.

1. In a surgical electrode comprising
   a. an electrically conductive wire,
   b. a *metal* needle *having a pointed end and a blunt end*, said needle being attached *adjacent its blunt end* to and in electrical contact with said wire and having a substantially straight shank portion adjacent the point of attachment to said wire, and
   c. a non-conductive coating over the exterior surface of the wire electrically insulating said wire over a major portion of the length thereof, the improvement comprising providing a weakened zone in the needle adjacent the straight shank portion of said needle, *said electrically conductive wire terminating between said blunt end and said weakened zone* whereby said needle may be readily broken at said weakened zone *without said electrically conductive wire extending outwardly beyond said straight shank portion to thereby facilitate connection of said straight shank portion to an electrical device, including to a pacemaker or the like.*

10. In a surgical electrode comprising
    a. an electrically conductive wire,
    b. a first *metal* eyeless needle and a second *metal* eyeless needle attached to either end of said wire and in electrical contact therewith, at least one eyeless needle having a *pointed end and a blunt end, said at least one needle being attached adjacent its blunt end to and in electrical contact with said wire, said at least one needle having* a substantially straight shank portion at least about 1 cm. long adjacent the point of attachment to said wire, and
    c. a non-conductive coating over the exterior surface of the wire electrically insulating said wire over a major portion of the length thereof, the improvement comprising providing in the needle having a straight shank portion a weakened zone adjacent said straight shank portion, *said electrically conductive wire terminating between said blunt end and said weakened zone* whereby the needle may be readily broken by a bending moment applied about the weakened zone *without said electrically conductive wire extending outwardly beyond said straight shank portion to thereby facilitate connection of said straight shank portion to an electrical device, including to a pacemaker or the like.*

*11. An electrode of claim 1 wherein the weakened zone is closer to the blunt end of said needle than to the pointed end thereof.*

*12. An electrode of claim 1 wherein the weakened zone is at least about 1 cm. from the blunt end of said needle.*

*13. An electrode of claim 1 in which said needle has a cylindrical portion between the pointed and blunt ends thereof, and wherein said weakened zone is located in said cylindrical portion.*

*14. An electrode of claim 13 wherein said weakened zone is defined by a reduced diameter portion in said cylindrical portion.*

* * * * *